United States Patent
Shimizu et al.

[11] Patent Number: 5,856,866
[45] Date of Patent: Jan. 5, 1999

[54] IMAGE PRODUCING APPARATUS

[75] Inventors: Hitoshi Shimizu; Yukinori Nishioka, both of Kanagawa, Japan

[73] Assignee: Fuji Photo Film Co., Ltd., Kanagawa-ken, Japan

[21] Appl. No.: 960,598

[22] Filed: Oct. 30, 1997

[30]  Foreign Application Priority Data

Oct. 31, 1996 [JP] Japan ................................. 8-289747
Mar. 31, 1997 [JP] Japan ................................. 9-079441

[51] Int. Cl.⁶ ........................ G01N 21/64; G01N 27/447
[52] U.S. Cl. ...................... 356/73; 356/318; 356/417; 356/344; 250/458.1; 422/52
[58] Field of Search ................................. 356/317, 318, 356/344, 417, 73; 250/458.1, 459.1, 461.1, 461.2, 361 C; 422/52

[56]  References Cited

U.S. PATENT DOCUMENTS 4,184,196 1/1980 Moret et al. ............................. 433/29
5,304,809 4/1994 Wickersheim ...................... 250/458.1
5,653,539 8/1997 Rosengaus ......................... 250/458.1

Primary Examiner—F. L. Evans
Attorney, Agent, or Firm—Sughrue, Mion, Zinn, Macpeak & Seas, PLLC

[57]  ABSTRACT

An image producing apparatus includes at least one light emitting diode stimulating ray source, a filter for cutting a stimulating ray emitted from the at least one light emitting diode stimulating ray source and allowing only fluorescent light generated by stimulation of a fluorescent substance by the stimulating ray to pass therethrough, and a solid state image sensor for detecting the fluorescent light transmitted through the filter. According to the thus constituted image producing apparatus, it is possible to safely produce a fluorescent image at low cost.

20 Claims, 8 Drawing Sheets

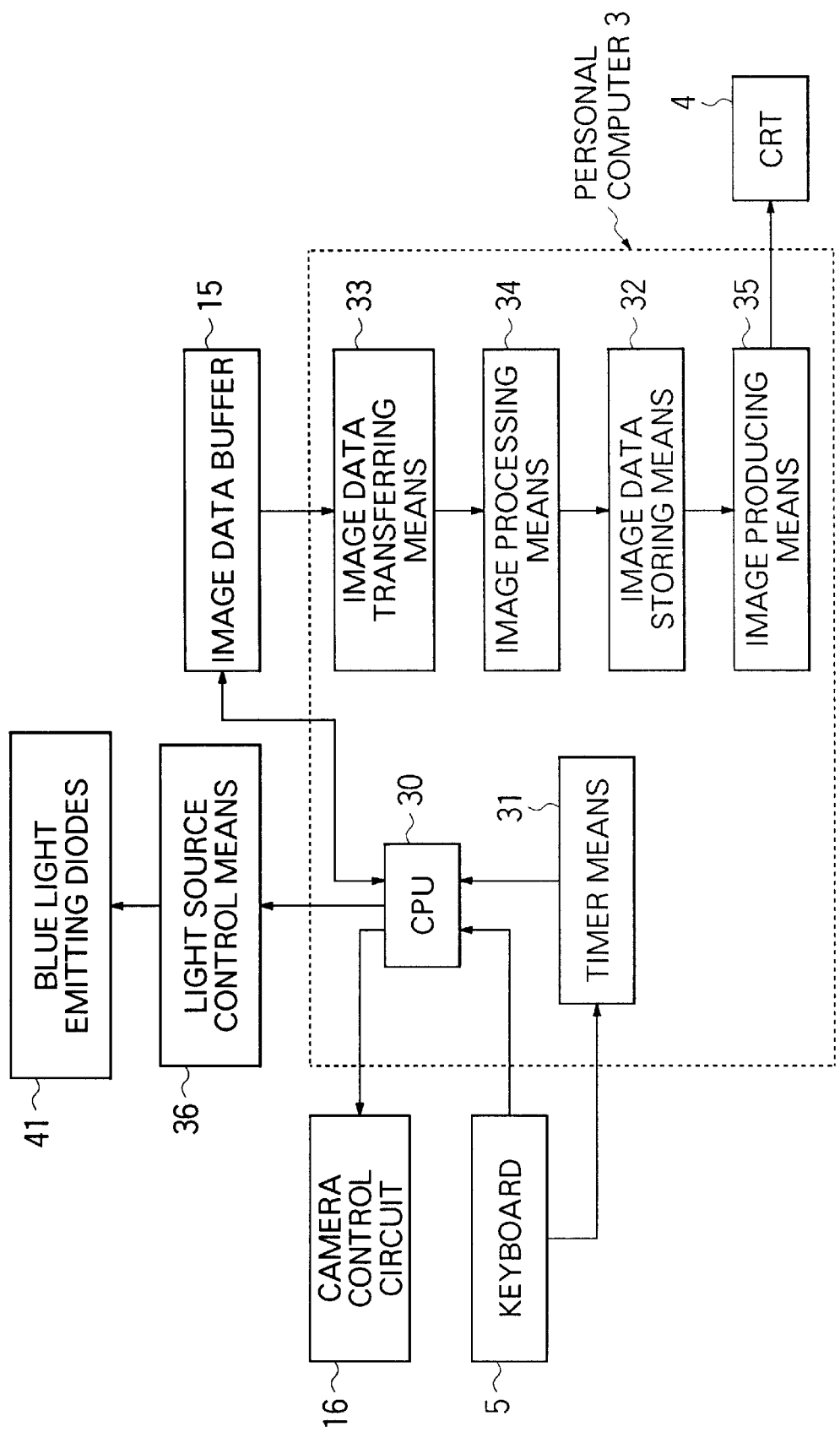

IMAGE PRODUCING APPARATUS

BACKGROUND OF THE INVENTION

The present invention relates to an image producing apparatus and, particularly, to such an apparatus which uses a solid state image sensor and can safely produce a fluorescent image at low cost.

DESCRIPTION OF THE PRIOR ART

A fluorescence system using a fluorescent substance as a labeling substance is known. According to this system, it is possible to study a genetic sequence, the expression level of a gene and the metabolism, absorption, excretion path and state of a substance introduced into a test mouse and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed or distributing a plurality of DNA fragments on a gel support containing fluorescent dye or dipping a gel support on which a plurality of DNA fragments have been distributed by means of electrophoresis in a solution containing fluorescent dye, thereby labeling the electrophoresis-distributed DNA fragments, exciting the fluorescent dye by a stimulating ray to cause it to release a fluorescent light, detecting the released fluorescent light to produce an image and detecting the distribution of the DNA on the gel support. This system can also perform a process including the steps of distributing a plurality of DNA fragments on a gel support by means of electrophoresis, denaturing the DNA, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release a fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substrate, transforming the fluorescent substrate to a fluorescent substance having a fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance unlike an autoradiography.

Since most substances emit fluorescent light upon being irradiated with ultraviolet rays, the image producing apparatus used in this fluorescent detecting system generally uses an ultraviolet ray source for emitting ultraviolet rays having a wavelength of 250 to 400 nm, particularly 365 nm or 315 nm, as a stimulating ray source.

However, ultraviolet rays having a wavelength of 250 to 400 nm are harmful to the human body. When an ultraviolet ray source is used as a stimulating ray source, therefore, it is necessary to protect users from exposure to the ultraviolet rays. For this, it is necessary to take various protective measures, such as having the user wear UV-cut glasses, thereby increasing costs.

Particularly, in the fluorescent detection system, it is often necessary to electrophorese a specimen labeled with a fluorescent substance on a gel, view an obtained image, pick out a portion where a specific target substance is distributed by cutting or sucking it out, further process the portion and conduct various analyses. For carrying out such a process, the electrophoresed specimen is irradiated with ultraviolet rays to visualize an electrophoresis image and the user visually observes the electrophoresis image to find the portion where the specific target substance is distributed so as to be able to pick out the portion by cutting or sucking. The user therefore cannot avoid being exposed to the ultraviolet rays.

Further, a chemiluminescence detecting system is known, which comprises the steps of selectively labeling a fixed high molecular substance such as a protein or a nucleic acid sequence with a labeling substance which generates chemiluminescent emission when it contacts a chemiluminescent substance, contacting the high molecular substance selectively labeled with the labeling substance and the chemiluminescent substance, photoelectrically detecting the chemiluminescent emission in the wavelength of visible light generated by the contact of the chemiluminescent substance and the labeling substance, producing digital image signals, effecting image processing on the signals, reproducing a chemiluminescent image on a display means such as a CRT or a recording material such as a photographic film and obtaining information relating to the high molecular substance such as genetic information. This chemiluminescence detecting system is used for similar purposes to those of the fluorescent detecting system. Therefore, it is preferable for a single image producing apparatus to be able to produce both a fluorescent image by a fluorescence detecting system and a chemiluminescent image by a chemiluminescence detecting system.

In this connection, since chemiluminescent emission is weak, a specimen has to be kept in a space completely shielded from light for detecting chemiluminescent emission and producing a chemiluminescent image. However, the discharge tube used as an ultraviolet ray source in the fluorescence detecting system generates much heat and it is necessary to take measures for dispersing heat when the ultraviolet ray source is employed. As a result, it is difficult to keep a specimen in a space completely shielded from light and, therefore, it is difficult for a single image producing apparatus to produce both a fluorescent image by a fluorescence detecting system and a chemiluminescent image by a chemiluminescence detecting system.

SUMMARY OF THE INVENTION

It is therefore an object of the present invention to provide an image producing apparatus which uses a solid state image sensor and can safely produce a fluorescent image at low cost.

Another object of the present invention is to provide an image producing apparatus which can produce both a fluorescent image by the fluorescence detecting system and a chemiluminescent image by the chemiluminescence detecting system.

The above and other objects of the present invention can be accomplished by an image producing apparatus comprising at least one light emitting diode (LED) stimulating ray source, filter means for cutting a stimulating ray emitted from the at least one light emitting diode stimulating ray source and allowing only fluorescent light generated by stimulation of a fluorescent substance by the stimulating ray to pass therethrough, and a solid state image sensor for detecting the fluorescent light transmitted through the filter means.

In a preferred aspect of the present invention, the at least one light emitting diode stimulating ray source is constituted so as to emit a stimulating ray whose center wavelength is between 400 nm and 700 nm.

In a further preferred aspect of the present invention, the at least one light emitting diode stimulating ray source is constituted so as to emit a stimulating ray whose center wavelength is between 400 nm and 550 nm.

In a further preferred aspect of the present invention, the at least one light emitting diode stimulating ray source is constituted as a blue light emitting diode for emitting a stimulating ray whose center wavelength is between 400 nm and 500 nm.

In a further preferred aspect of the present invention, the at least one light emitting diode stimulating ray source comprises a light emitting diode base plate including a plurality of light emitting diode stimulating ray sources and a diffusion plate positioned on the light emitting diode base plate and on which a gel including an electrophoresed specimen can be placed.

In a further preferred aspect of the present invention, the at least one light emitting diode stimulating ray source comprises a light emitting diode base plate including a plurality of light emitting diode stimulating ray sources and a diffusion plate positioned on the light emitting diode base plate and on which an electrophoresis tank for accommodating a gel containing a specimen to be electrophoresed can be placed.

In a further preferred aspect of the present invention, the filter means is detachable.

In a further preferred aspect of the present invention, the solid state image sensor is constituted as a cooled CCD.

In a further preferred aspect of the present invention, an image intensifier is provided in front of the solid state image sensor.

In the present invention, examples of the fluorescent dye stimulable by light emitted from the light emitting diode stimulating ray source and having a wavelength of 400 to 700 nm include Fluorescein (C.I. No. 45350), Fluorescein-X indicated by the structural formula (1) shown below, YOYO-1 indicated by the structural formula (2), TOTO-1 indicated by the structural formula (3), YO-PRO-1 indicated by the structural formula (4), Cy-3 (registered trademark) indicated by the structural formula (5), Nile Red indicated by the structural formula (6), BCECF indicated by the structural formula (7), Rhodamine 6G (C.I. No. 45160), Acridine Orange (C.I. No. 46005), SYBR Green ($C_2H_6OS$), Ethidium Bromide indicated by the structural formula (9), Texas Red indicated by the structural formula (10), Propidium Iodide indicated by the structural formula (11), POPO-3 indicated by the structural formula (12), Quantum Red, R-Phycoerrythrin, Red 613, Red 670, Fluor X, FAM, AttoPhos, Bodipy phosphatidylcholine, SNAFL, Calcium Green, Fura Red, Fluo 3, AllPro, NBD phosphoethanolamine, Carboxyrhodamine (R6G), JOE, HEX, Ethidium homodimer, Lissamine rhodamine B peptide, Cy-5 (registered trademark) indicated by the structural formula (8), Allphycocyanin and the like.

In the present invention, examples of the fluorescent dye stimulable by light emitted from the light emitting diode stimulating ray source and having a wavelength of 400 to 550 nm include Fluorescein (C.I. No. 45350), Fluorescein-X indicated by the structural formula (1) shown below, YOYO-1 indicated by the structural formula (2), TOTO-1 indicated by the structural formula (3), YO-PRO-1 indicated by the structural formula (4), Cy-3 (registered trademark) indicated by the structural formula (5), Nile Red indicated by the structural formula (6), BCECF indicated by the structural formula (7), Rhodamine 6G (C.I. No. 45160), Acridine Orange (C.I. No. 46005), SYBR Green ($C_2H_6OS$), Ethidium Bromide indicated by the structural formula (9), Texas Red indicated by the structural formula (10), Propidium Iodide indicated by the structural formula (11), POPO-3 indicated by the structural formula (12), Quantum Red, R-Phycoerrythrin, Red 613, Red 670, Fluor X, FAM, AttoPhos, Bodipy phosphatidylcholine, SNAFL, Calcium Green, Fura Red, Fluo 3, AllPro, NBD phosphoethanolamine, Carboxyrhodamine (R6G), JOE, HEX, Ethidium homodimer, Lissamine rhodamine B peptide and the like.

In the present invention, examples of the fluorescent dye stimulable by light emitted from the light emitting diode stimulating ray source and having a wavelength of 400 to 500 nm include Fluorescein (C.I. No. 45350), Fluorescein-X indicated by the structural formula (1) shown below, YOYO-1 indicated by the structural formula (2), TOTO-1 indicated by the structural formula (3), YO-PRO-1 indicated by the structural formula (4), Cy-3 (registered trademark) indicated by the structural formula (5), Nile Red indicated by the structural formula (6), BCECF indicated by the structural formula (7), Rhodamine 6G (C.I. No. 45160), Acridine Orange (C.I. No. 46005), SYBR Green ($C_2H_6OS$), Quantum Red, R-Phycoerrythrin, Red 613, Red 670, Fluor X, FAM, AttoPhos, Bodipy phosphatidylcholine, SNAFL, Calcium Green, Fura Red, Fluo 3, AllPro, NBD phosphoethanolamine and the like.

Structural Formula

The above and other objects and features of the present invention will become apparent from the following description made with reference to the accompanying drawings.

BRIEF DESCRIPTION OF THE DRAWINGS

FIG. 9 is a block diagram of a personal computer and the peripheral devices thereof.

DESCRIPTION OF THE PREFERRED EMBODIMENT

Figure 1:
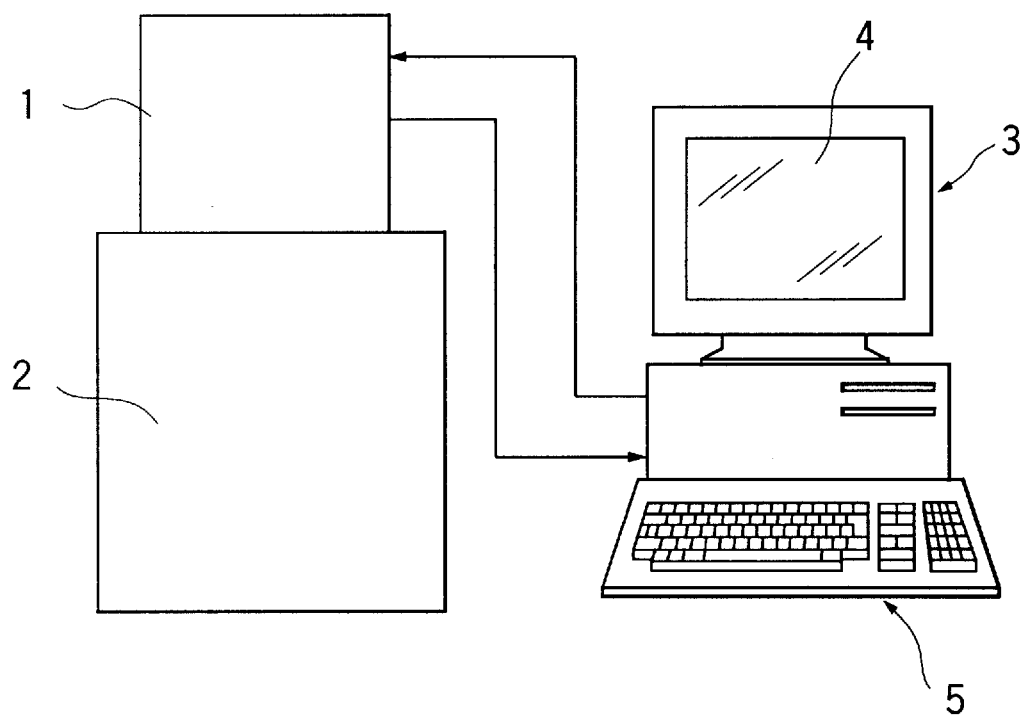
FIG. 1 is a schematic front view showing an image producing apparatus which is an embodiment of the present invention.

FIG. 1 is a schematic front view showing an image producing apparatus which is an embodiment of the present invention. The image producing apparatus according to this embodiment is adapted to detect chemiluminescence emission generated by contacting a chemiluminescent substance with a labeling substance and a fluorescent light emitted from an image carrier carrying an image of a fluorescent substance and produce a visual image.

As shown in FIG. 1, the image producing apparatus includes an imaging device 1, a dark box 2 and a personal computer 3. The personal computer 3 is equipped with a CRT 4 and a keyboard 5.

Figure 2:
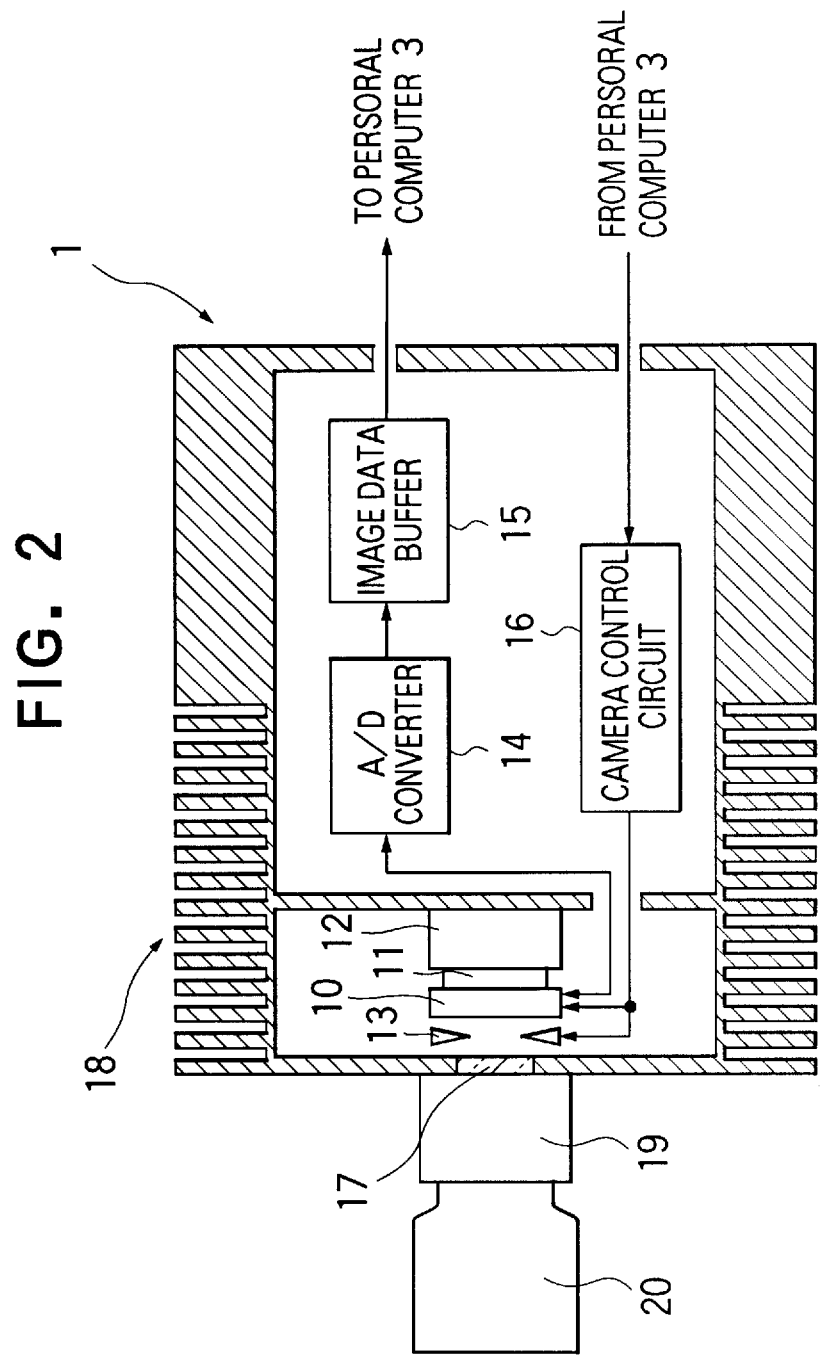
FIG. 2 is a schematic longitudinal cross sectional view showing an imaging device.

FIG. 2 is a schematic longitudinal cross sectional view showing the imaging device 1.

As shown in FIG. 2, the imaging device 1 includes a CCD (charge coupled device) 10, a heat transfer plate 11 made of metal such as aluminum, a Peltier element 12, a shutter 13 positioned in front of the CCD 10, an A/D converter 14 for converting analog image data produced by the CCD 10 to digital image data, an image data buffer 15 for temporarily storing image data digitized by the A/D converter 14 and a camera control circuit 16 for controlling the operation of the imaging device 1. An opening portion formed between the imaging device and the dark box 2 is closed by a glass plate 17 and the periphery of the imaging device 1 is formed with heat dispersion fins 18 over substantially half its length for dispersing heat released from the Peltier element 11.

An image intensifier 19 disposed in the dark box 2 is provided in front of the glass plate 17 and a camera lens 20 is mounted on the front surface of the image intensifier 19.

Figure 3:
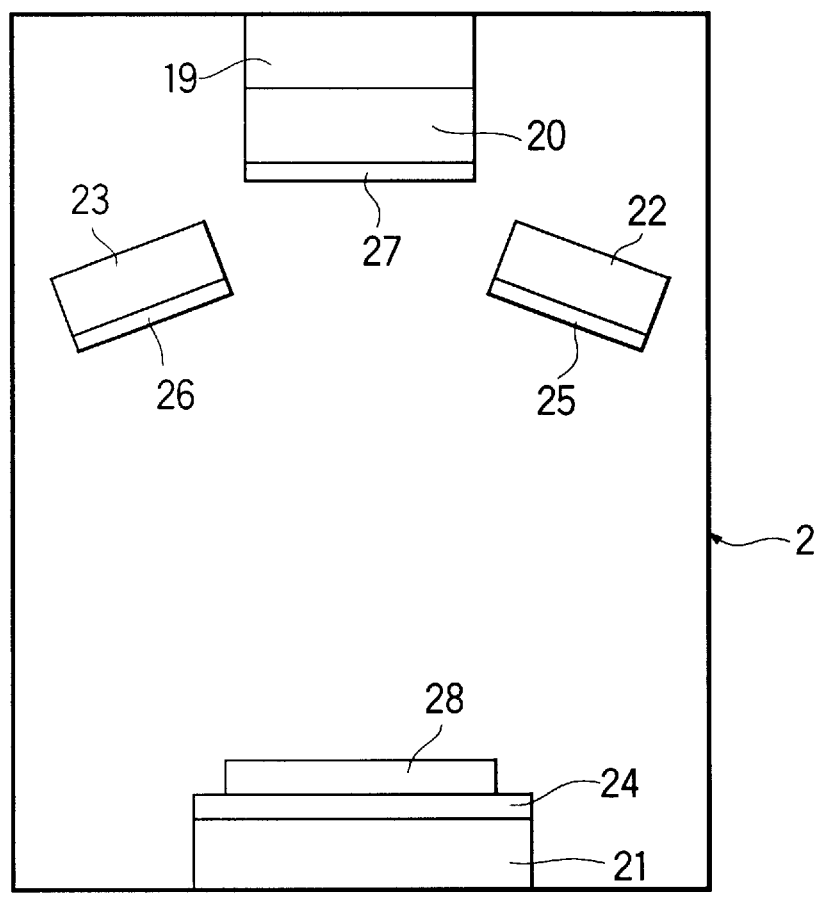
FIG. 3 is a schematic vertical cross sectional view showing a dark box.

FIG. 3 is a schematic longitudinal cross sectional view of the dark box 2.

As shown in FIG. 3, the dark box 2 is equipped with a first blue light emitting diode stimulating ray source 21 for emitting a stimulating ray whose center wavelength is 450 nm and a second blue light emitting diode stimulating ray source 22 and a third blue light emitting diode stimulating ray source 23 are provided obliquely above the first blue light emitting diode stimulating ray source 21, each being adapted for emitting a stimulating ray whose center wavelength is 450 nm. A filter 24 is adhered to the upper surface of the first blue light emitting diode stimulating ray source 21 and filters 25, 26 are respectively adhered to the front surfaces of the second blue light emitting diode stimulating ray source 22 and the third blue light emitting diode stimulating ray source 23. The filters 24, 25, 26 cut light of wavelengths other than one in the vicinity of 450 nm and harmful to the stimulation of a fluorescent substance and transmit light having a wavelength in the vicinity of 450 nm. A filter 27 for cutting the stimulating ray having a wavelength in the vicinity of 450 nm is detachably provided on the front surface of the camera lens 20. In FIG. 3, the reference numeral 28 designates an image carrier carrying an image of fluorescent substance.

Figure 4:
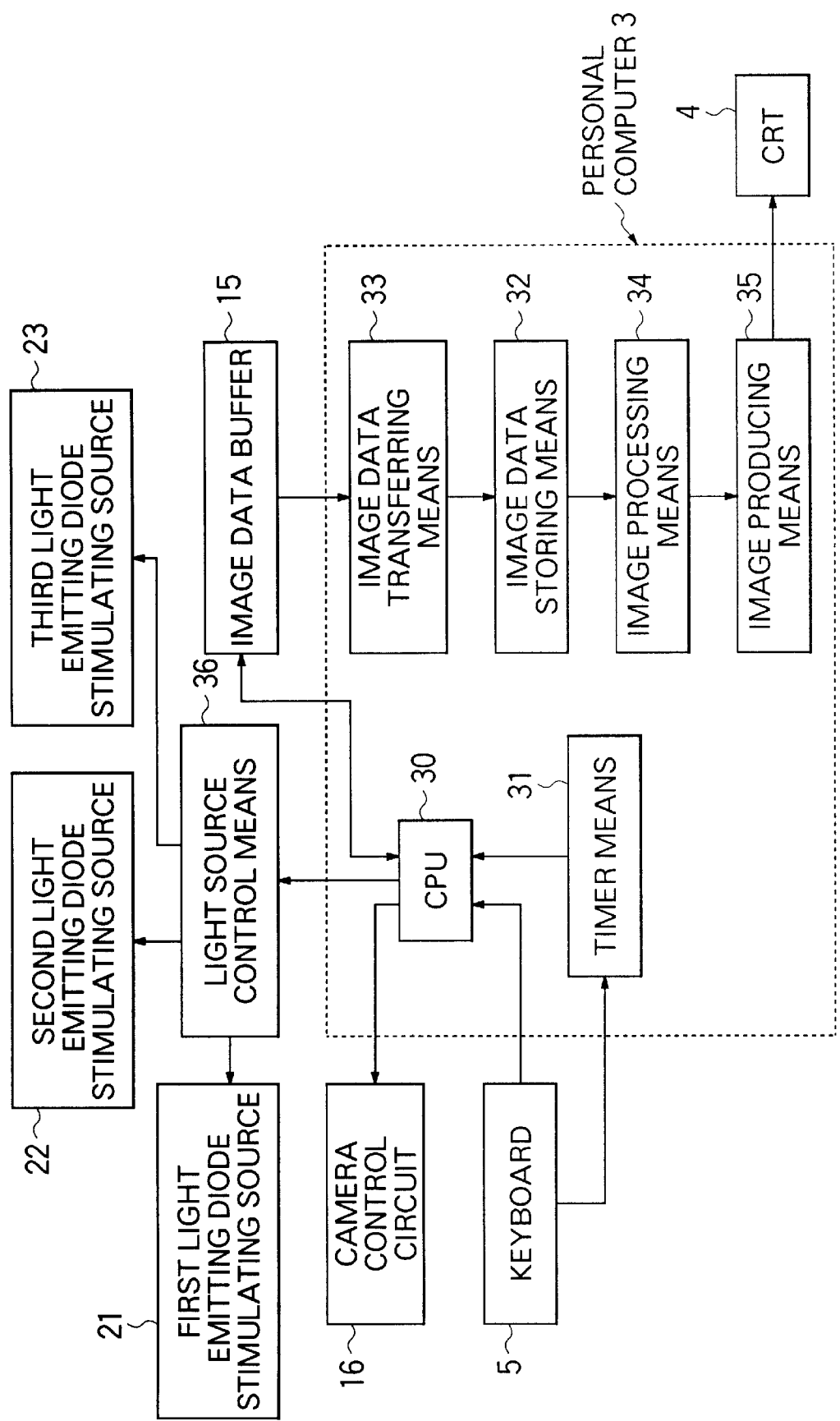
FIG. 4 is a block diagram of a personal computer and peripheral devices thereof.

FIG. 4 is a block diagram of the personal computer 3 and the peripheral devices thereof.

As shown in FIG. 4, the personal computer 3 includes a CPU 30 for controlling the exposure of the CCD 10, a timer means 31 for storing an exposure time input by a user, an image data storing means 32 for storing image data produced by the imaging device 1, an image data transferring means 33 for transferring the image data produced by the imaging device 1 to the image data storing means 32, an image processing means 34 for effecting image processing on the image data stored in the image data storing means 32 and an image producing means 35 for producing a visual image on the screen of the CRT 4 based on the image data stored in the image data storing means 32. The first blue light emitting diode stimulating ray source 21, the second blue light emitting diode stimulating ray source 22 and the third blue light emitting diode stimulating ray source 23 are controlled by a light source control means 36 and an instruction signal can be input via the CPU 30 to the light source control means 36 through the keyboard 5.

The thus constituted image producing apparatus according to this embodiment detects fluorescent light from the image carrier 28 carrying an image of a fluorescent substance and produces a visual image in the following manner.

When the user inputs an exposure time T during which the CCD 10 is to be exposed through the keyboard 5, the exposure time T is stored in the timer means 31. The image carrier 28, which is a specimen, is then placed on the filter 24 and lens focus is adjusted by the user. After the dark box 2 has been closed, the user inputs an exposure start signal through the keyboard 5. The first blue light emitting diode stimulating ray source 21 alone or the second blue light emitting diode stimulating ray source 22 and the third blue light emitting diode stimulating ray source 23 are turned on by the light source control means 36, thereby emitting a stimulating ray toward the image carrier 28.

Light components of wavelengths not in the vicinity of 450 nm are cut by the filters 24, 25, 26 from the stimulating rays emitted from the first blue light emitting diode stimulating ray source 21 alone or the second blue light emitting diode stimulating ray source 22 and the third blue light emitting diode stimulating ray source 23. As a result, the fluorescent substance contained in the image carrier 28 is stimulated by light having a wavelength in the vicinity of 450 nm, thereby emitting fluorescent light.

The fluorescent light emitted from the fluorescent substance contained in the image carrier 28 enters the photo-electrical surface of the image intensifier 19 via the filter 27 and the camera lens 20 and amplified so that an image is formed on the fluorescent surface of the image intensifier 19. The CCD 10 of the imaging device 1 receives light from the image formed on the fluorescent surface of the image intensifier 19 to convert electric charges and accumulates them. Since light components having wavelengths in the vicinity of 450 nm are cut by the filter 27, only fluorescent light emitted from the fluorescent substance contained in the image carrier 28 is received by the CCD 10 of the imaging device 1.

When the exposure time has passed, the CPU 30 outputs an exposure completion signal to the imaging device 1 and causes the CCD 10 to transfer electric charges accumulated therein to the A/D converter 14 and the A/D converter 14 to produce digital image data. At the same time, the CPU 30 outputs a data transfer signal to the image data transferring means 33 to store the digital image data produced by the imaging device 1 in the image data storing means 32.

Afterward, when the user inputs an image producing signal and an image processing signal through the keyboard 5, the digital image data stored in the image data storing means 32 are read out and input to the image processing means 34. In accordance with the input image processing signal, the image processing means 34 effects image processing on the read out digital image data and a visual image is produced on the screen of the CRT 4 based on the image-processed digital image data from the image producing means 35.

A chemiluminescent image is produced in the same manner as a fluorescent image except that the filter 27 is removed and the first blue light emitting diode stimulating ray source 21, the second blue light emitting diode stimulating ray source 22 and the third blue light emitting diode stimulating ray source 23 are kept to be off, chemiluminescent emission emitted from the image carrier 28 is photoelectrically detected by the CCD 10 via the camera lens 20 and the image intensifier 19 to produce image data and a chemiluminescent image is produced on the screen of the CRT 4. The CPU 30 is constituted so as not to output an operation signal to the light source control means 36 when an instruction signal requesting the production of a chemiluminescent image is input together with an exposure start signal through the keyboard 5.

According to this embodiment, since the first blue light emitting diode stimulating ray source 21, the second blue light emitting diode stimulating ray source 22 and the third blue light emitting diode stimulating ray source 23 are used as a stimulating source for stimulating a fluorescent substance contained in the image carrier 28, it is unnecessary to take measures to prevent the user from being exposed to ultraviolet rays and, therefore, it is possible to safely produce a fluorescent image at low cost.

Further, according to this embodiment, since the light emitting diode stimulating ray sources 21, 22, 23 used generate less heat than an ultraviolet ray source, it is unnecessary to take measures for heat dispersion. Therefore, since the dark box 2 can be completely shielded from light and extremely weak chemiluminescent emission can be detected, it is possible to produce a fluorescent image by the fluorescence detecting system and a chemiluminescent image by the chemiluminescent detecting system using a single image producing apparatus.

Figure 5:
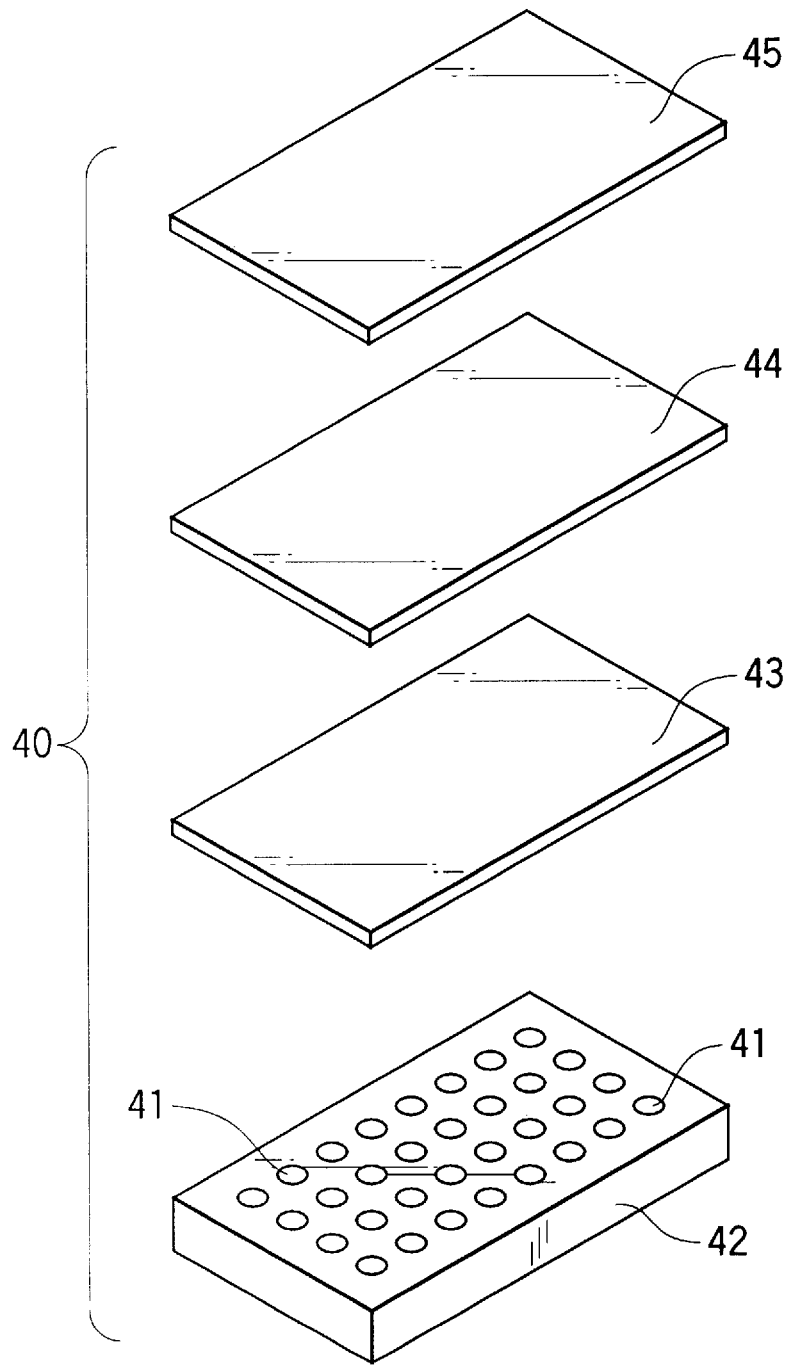
FIG. 5 is a schematic exploded view showing a fluorescent image visualizing device which is another embodiment of the present invention.
Figure 6:
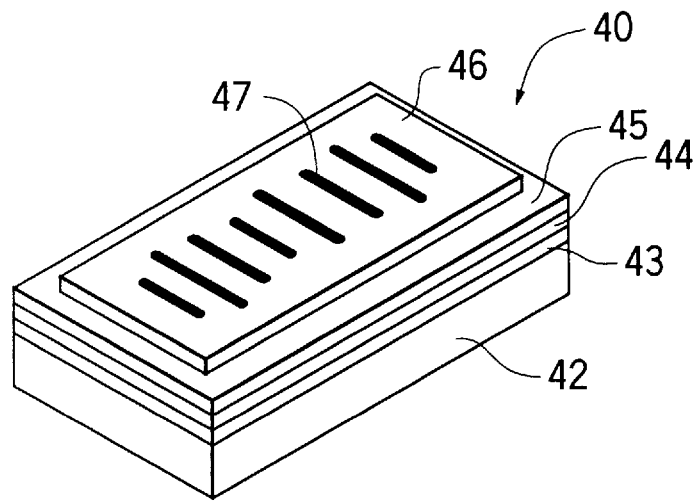
FIG. 6 is a schematic perspective view showing a fluorescent image visualizing device which is another embodiment of the present invention.

FIG. 5 is a schematic exploded view showing a fluorescent image visualizing device which is another embodiment of the present invention and FIG. 6 is a schematic perspective view thereof.

As shown in FIGS. 5 and 6, the fluorescent image visualizing device 40 includes a blue light emitting diode array base plate 42 provided with a plurality of blue light emitting diodes 41 for emitting a stimulating ray whose center wavelength is 450 nm, a bandpass filter 43 placed on the blue light emitting diode array base plate 42, a diffusion plate 44 made of opal glass, slightly opaque acrylic resin or the like, and a transparent cover glass 45 placed on the diffusion plate 44. A gel containing specimen labeled with a fluorescent substance and electrophoresed is placed on the transparent cover glass 45. The bandpass filter 43 is provided for improving the contrast of a fluorescent image and the transparent cover glass 45 is provided for preventing the diffusion plate 44 from being damaged when a band portion of a target substance is cut out with a knife.

When the thus constituted fluorescent image visualizing device 40 is located in a slightly dark ambience and the plurality of blue light emitting diodes 41 of the blue light emitting diode array base plate 42 are turned on, blue light is emitted from the plurality of blue light emitting diodes 41. The blue light passing through the bandpass filter 43 is converted to non-directional light by passing through the diffusion plate 44 and impinges on the gel 46 via the transparent cover glass 45. The gel 46 is formed with bands 47 of the specimen labeled with a fluorescent substance and electrophoresed and the fluorescent substance is stimulated by light impinging on the gel and having a wavelength in the vicinity of 450 nm, thereby emitting fluorescent light from the bands 47. The thus emitted fluorescent light can be viewed with the eyes and, therefore, an electrophoresis image of the specimen can be visualized in this manner. In this case, if the user wears sun glasses for cutting light having the wavelength of the stimulating ray emitted from the blue light emitting diodes 41, the bands can be viewed with the eyes, even if the amount of light emitted from the fluorescent substance is small.

According to this embodiment, it is possible to safely view the bands 47 of the specimen labeled with a fluorescent substance and electrophoresed on the gel 46 and analyze a target substance by finding a band portion where the target substance is distributed, picking out it by means of cutting it out with a knife, sucking it out or the like and further processing it.

Figure 7:
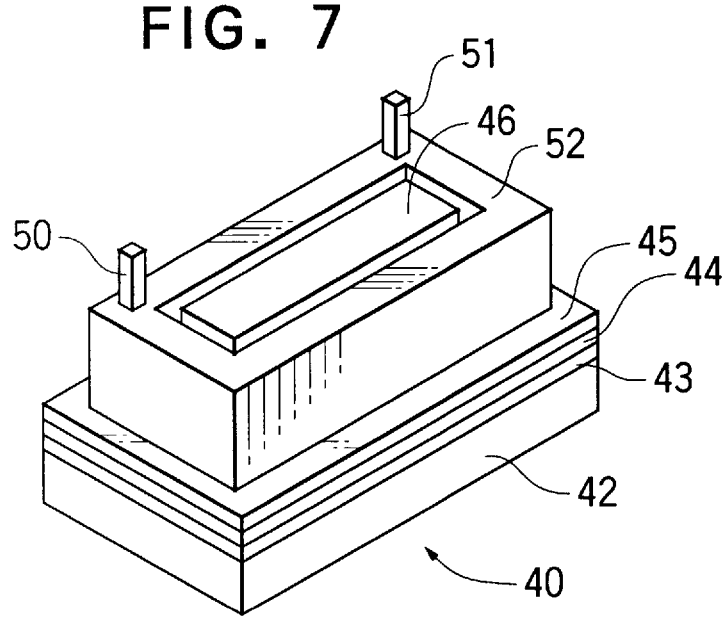
FIG. 7 is a schematic perspective view showing a fluorescent image visualizing device which is a further embodiment of the present invention.

FIG. 7 is a schematic perspective view showing a fluorescent image visualizing device which is a further embodiment of the present invention.

As shown in FIG. 7, the fluorescent image visualizing device 40 according to this embodiment includes a blue light emitting diode array base plate 42 provided with a plurality of blue light emitting diodes (not shown) for emitting a stimulating ray whose center wavelength is 450 nm, a bandpass filter 43 placed on the blue light emitting diode array base plate 42, a diffusion plate 44 and a transparent cover glass 45 placed on the diffusion plate 44. In this embodiment, an electrophoresis tank 52 provided with electrodes 50, 51 is placed on the transparent cover glass 45 and a gel 46 is set in the electrophoresis tank 52 so that a specimen labeled with a fluorescent substance can be electrophoresed therein.

The fluorescent image visualizing device 40 is located in a slightly dark ambience and voltage is applied to the gel 46 via the electrodes 50, 51, thereby electrophoresing a specimen in the electrophoresis tank 52. The plurality of blue light emitting diodes of the blue light emitting diode array base plate 42 are then turned on and, similarly to in the previous embodiment, the electrophoresis image is visualized. By viewing the visualized image, the band portion where the target substance is distributed can be found and the target substance can be analyzed by picking it out by cutting with a knife, sucking or the like, and further processing it.

According to this embodiment, the specimen can be electrophoresed and an electrophoresis image can be safely visualized in situ.

Figure 8:
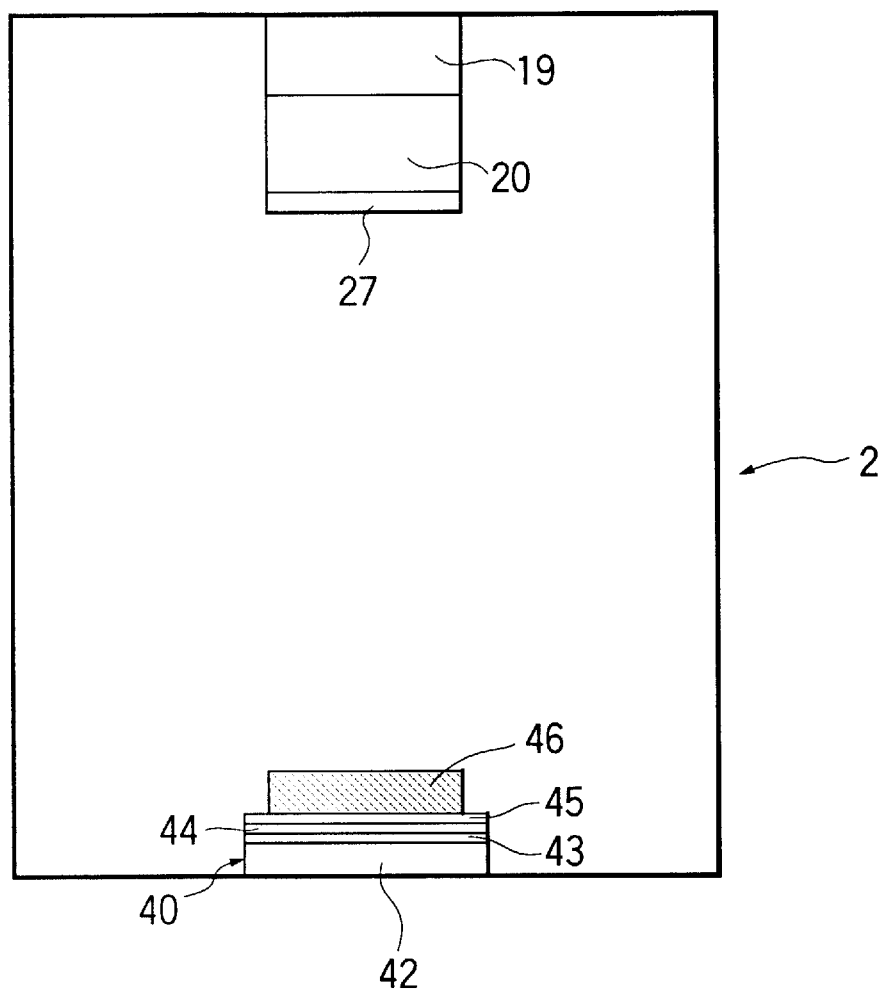
FIG. 8 is a schematic vertical cross sectional view showing a dark box of an image producing apparatus which is a further embodiment of the present invention.

FIG. 8 is a schematic vertical cross sectional view showing a dark box of an image producing apparatus which is a further embodiment of the present invention.

As shown in FIG. 8, the dark box 2 of the image producing apparatus according to this embodiment is equipped with a fluorescent image visualizing device 40 shown in FIGS. 5 and 6 instead of the first blue light emitting diode stimulating ray source 21 and the filter 24 and the second blue light emitting diode stimulating ray source 22 and the third blue light emitting diode stimulating ray source 23 are not provided. Specifically, the image producing apparatus includes a blue light emitting diode array base plate 42 provided with a plurality of blue light emitting diodes 41 for emitting a stimulating ray whose center wavelength is 450 nm, a bandpass filter 43 placed on the blue light emitting diode array base plate 42, a diffusion plate 44 made of opal glass, slightly opaque acrylic resin or the like, and a transparent cover glass 45 placed on the diffusion plate 44. A gel containing a specimen labeled with a fluorescent substance and electrophoresed is placed on the transparent cover glass 45. The filter 27 is secured to the front surface of the camera lens 20 for cutting light of a wavelength equal to that of the stimulating ray emitted from the plurality of blue light emitting diodes 41.

FIG. 9 is a block diagram of a personal computer and the peripheral devices thereof.

As shown in FIG. 9, the personal computer 3 includes a CPU 30 for controlling the exposure of the CCD 10, a timer means 31 for storing an exposure time input by a user, an image data transferring means 33 for reading out image data produced by the imaging device from the image data buffer 15, an image processing means 34 for effecting image processing on the image data read out by the image data transferring means 33 and storing them in an image data storing means 32, and an image producing means 35 for displaying a visual image on the screen of the CRT 4 based on the image data stored in the image data storing means 32. The plurality of blue light emitting diodes 41 are controlled by the light source control means 36 and an instruction signal can be input via the CPU 30 to the light source control means 36 through the keyboard 5. The CPU 30 is adapted to output various signals to the camera control circuit 16 of the imaging device 1.

In this embodiment, when a user inputs a lens focus adjusting signal through the keyboard 5, the CPU 30 outputs a lens focus adjusting mode signal to the camera control circuit 16. When the camera control circuit 16 receives the lens focus adjusting mode signal, it controls a reading operation control circuit (not shown) to cause it to transfer image data stored in the CCD 10 in the form of electric charges every predetermined time period.

Prior to reading a fluorescent image, the gel 46 containing a specimen labeled with a fluorescent substance and electrophoresed is placed on the transparent cover glass 45 by the user and the camera lens 20 is operated to adjust the lens focus. When the lens focus adjustment has been completed, the dark box 2 is closed. Afterward, when the user inputs an exposure start signal through the keyboard 5, the plurality of blue light emitting diodes 41 are turned on by the light source control means 36 and a stimulating ray is emitted toward the gel 46. At the same time, the exposure start signal is input to the camera control circuit 16 and the shutter 13 is opened to start the exposure of the CCD 10.

Bands of the specimen labeled by fluorescent substance and electrophoresed are formed on the gel 46 and when they are irradiated with the stimulating ray emitted from the plurality of blue light emitting diodes 41, the fluorescent substance is stimulated to emit fluorescent light. The fluorescent light emitted from the fluorescent substance impinges on the fluorescent surface of the image intensifier 19 via the filter 27 and the camera lens 20 to form an image. The CCD 10 receives light from the image formed on the fluorescent surface of the image intensifier 19, converts it to electric charges and accumulates the charges. Since light having a wavelength equal to that of the stimulating ray is cut by the filter 27, only fluorescent light emitted from the fluorescent substance in the specimen contained in the gel 46 is received by the CCD 10 of the imaging device 1.

When a predetermined exposure time has passed, the CPU 30 outputs an exposure completion signal to the camera control circuit 16 of the imaging device 1. When the camera control circuit 16 receives the exposure completion signal from the CPU 30, it causes the CCD 10 to transfer analog image data accumulated therein in the form of electric charges to the AND converter 14 and causes the A/D converter 14 to digitize them. The digital image data are temporarily stored in the image data buffer 15. At the same time, the CPU 30 outputs a data transferring signal to the image transferring means 33 and causes it to read out the digital image data temporarily stored in the image data buffer 15 of the imaging device and to input them to the image processing means 34. The image processing means 34 effects image processing on the image data input from the image data transferring means 33 and stores them in the image data storing means 32.

Afterward, when the user inputs an image producing signal through the keyboard 5, the digital image data stored in the image data storing means 32 are read out by the image producing means 35 and, based on the read out image data, a fluorescent image containing bands of the specimen is displayed on the screen on the CRT 4.

According to this embodiment, it is possible to visualize an electrophoresis image of the specimen on the screen of the CRT 4 by the imaging device 1 including the CCD 10, find a band portion where the target substance is distributed, pick out the portion by cutting it out with a knife, sucking it out or the like, further process it and analyze the target substance.

The present invention has thus been shown and described with reference to specific embodiments. However, it should be noted that the present invention is in no way limited to the details of the described arrangements but changes and modifications may be made without departing from the scope of the appended claims.

For example, in the above described embodiments shown in FIGS. 1 to 4 and 8 and 9, although the CCD 10 is used, instead of the CCD 10, an other type of solid state image sensor such as a CID (Charge Injection Device), PDA (Photo-Diode Array) or MOS type imaging element may be used.

Further, in the above described embodiments shown in FIGS. 1 to 4 and 8 and 9, although the image intensifier 19 is provided in front of the imaging device 1, it is not absolutely necessary to provide the image intensifier 19.

Moreover, in the above described embodiments shown in FIGS. 1 to 4 and 8 and 9, although the imaging device 1 includes the Peltier element 12 for cooling the CCD 10 and the heat dispersion fins 18 on the periphery of the imaging device 1 for dispersing heat emitted from the Peltier element 12, it is not absolutely necessary to provide the Peltier element 12 and the heat dispersion fins 18 and they may be omitted depending on the intensity of fluorescent light emitted from fluorescent substance.

Furthermore, in the above described embodiment shown in FIGS. 1 to 4, although the first blue light emitting diode stimulating ray source 21, the second blue light emitting diode stimulating ray source 22 and the third blue light emitting diode stimulating ray source 23 are provided in the dark box 2, only the first blue light emitting diode stimulating ray source 21, or only the second blue light emitting diode stimulating ray source 22 and the third blue light emitting diode stimulating ray source 23 may be provided.

Further, the first blue light emitting diode stimulating ray source 21, the second blue light emitting diode stimulating ray source 22, the third blue light emitting diode stimulating ray source 23 and the blue light emitting diodes 41 employed in the above described embodiments are each adapted to emit stimulating rays whose center wavelength is 450 nm, because many kinds of fluorescent substances used in fluorescent detection systems are designed to be effectively stimulated by an argon laser source for emitting a laser beam having a wavelength of 480 nm. However, a light emitting diode stimulating ray source for emitting light whose center wavelength is in the range between 400 and 700 nm may be employed depending on the kind of fluorescent substance.

Moreover, in the above described embodiment shown in FIGS. 1 to 4, although the exposure time T is set by the user, an exposure time T may be automatically determined by determining exposure times T in accordance with the kinds of image carrier 28 and the kinds of fluorescent substance in advance, storing them in the personal computer 3 and inputting the kind of image carrier 28 or the kind of fluorescent substance through the keyboard 5.

Furthermore, in the above described embodiment shown in FIGS. 1 to 4, when an exposure start signal is input through the keyboard 5, the first blue light emitting diode stimulating ray source 21 alone or the second blue light emitting diode stimulating ray source 22 and the third blue light emitting diode stimulating ray source 23 are turned on by the light source control means 36. However, it is not absolutely necessary to constitute the light source control means 36 so as to be controlled by the personal computer 3 and the light source control means 36 may be manually operated.

Further, in the above described embodiment shown in FIGS. 1 to 4, the filter 27 for cutting light having a wavelength in the vicinity of 450 nm is detachably mounted on the front surface of the camera lens 20 and the image producing apparatus is constituted so as to be able to detect extremely weak chemiluminescent emission and produce a chemiluminescent image when the filter 27 is removed. However, the image producing apparatus may be constituted so as to produce only a fluorescent image by the fluorescent detection system, in which case the filter 27 can be fixed to the front surface of the camera lens 20.

Moreover, in the above described embodiments shown in FIGS. 5 to 9, although the bandpass filter 43 is provided, it is not absolutely necessary to provide the bandpass filter 43.

Furthermore, in the above described embodiments shown in FIGS. 5 to 9, although the transparent cover glass 45 is provided on the diffusion plate 44, if the diffusion plate 44 is made of material resistant to damage, it is unnecessary to provide the transparent cover glass 45.

Further, in the above described embodiments shown in FIGS. 5 to 9, the electrophoresis image of the specimen is visualized, a portion where a target substance is distributed is found, picked out by cutting it out or sucking it out and further processed and the target substance is analyzed. However, it is sufficient to merely visualize the electrophoresis image of the specimen.

According to the present invention, it is possible to provide an image producing apparatus which uses a solid state image sensor and can safely produce a fluorescent image at low cost.

We claim:

1. An image producing apparatus having a fluorescence operating mode and a chemiluminescence operating mode, the apparatus comprising:
   at least one light emitting diode stimulating ray source,
   a solid state image sensor,
   filter means for allowing only fluorescent light generated by stimulation of a fluorescent substance by the stimulating ray to pass to the solid state image sensor in the fluorescence operating mode and allowing all light to pass to the solid state image sensor in the chemiluminescence operating mode,
   an enclosure restricting said stimulating ray and said fluorescent light from escaping.

2. An image producing apparatus in accordance with claim 1 wherein the at least one light emitting diode stimulating ray source is constituted so as to emit a stimulating ray whose center wavelength is between 400 nm and 700 nm.

3. An image producing apparatus in accordance with claim 2 wherein the at least one light emitting diode stimulating ray source is constituted so as to emit a stimulating ray whose center wavelength is between 400 nm and 550 nm.

4. An image producing apparatus in accordance with claim 3 wherein the at least one light emitting diode stimulating ray source is constituted as a blue light emitting diode for emitting a stimulating ray whose center wavelength is between 400 nm and 500 nm.

5. An image producing apparatus in accordance with claim 1 wherein the filter means comprises a filter disposed on an input face of the solid state image sensor in the fluorescence operating mode and not disposed on the input face of the solid state image sensor in the chemiluminescence operating mode.

6. An image producing apparatus in accordance with claim 2 wherein the filter means comprises a filter disposed on an input face of the solid state image sensor in the fluorescence operating mode and not disposed on the input face of the solid state image sensor in the chemiluminescence operating mode.

7. An image producing apparatus in accordance with claim 3 wherein the filter means comprises a filter disposed on an input face of the solid state image sensor in the fluorescence operating mode and not disposed on the input face of the solid state image sensor in the chemiluminescence operating mode.

8. An image producing apparatus in accordance with claim 4 wherein the filter means comprises a filter disposed on an input face of the solid state image sensor in the fluorescence operating mode and not disposed on the input face of the solid state image sensor in the chemiluminescence operating mode.

9. An image producing apparatus in accordance with claim 5 wherein the solid state image sensor is a cooled CCD.

10. An image producing apparatus in accordance with claim 6 wherein the solid state image sensor is a cooled CCD.

11. An image producing apparatus in accordance with claim 7 wherein the solid state image sensor is a cooled CCD.

12. An image producing apparatus in accordance with claim 8 wherein the solid state image sensor is a cooled CCD.

13. An image producing apparatus in accordance with claim 1 wherein an image intensifier is provided in front of the solid state image sensor.

14. An image producing apparatus in accordance with claim 5 wherein an image intensifier is provided in front of the solid state image sensor.

15. An image producing apparatus in accordance with claim 9 wherein an image intensifier is provided in front of the solid state image sensor.

16. An image producing apparatus comprising:
   at least one light emitting diode stimulating ray source;
   filter means for cutting a stimulating ray emitted from the at least one light emitting diode stimulating ray source, and allowing only fluorescent light generated by stimulation of a fluorescent substance by the stimulating ray to pass; and a solid state image sensor for detecting the fluorescent light transmitted through the filter means;

wherein the at least one light emitting diode stimulating ray source comprises a light emitting diode base plate including a plurality of light emitting diode stimulating ray sources and a diffusion plate positioned on the light emitting diode base plate and on which a gel including an electrophoresed specimen can be placed.

17. An image producing apparatus comprising:

at least one light emitting diode stimulating ray source;

filter means for cutting a stimulating ray emitted from the at least one light emitting diode stimulating ray source, and allowing only fluorescent light generated by stimulation of a fluorescent substance by the stimulating ray to pass; and a solid state image sensor for detecting the fluorescent light transmitted through the filter means;

wherein the at least one light emitting diode stimulating ray source is constituted as a blue light emitting diode for emitting a stimulating ray whose center wavelength is between 400 nm and 500 nm;

wherein the at least one light emitting diode stimulating ray source comprises a light emitting diode base plate including a plurality of light emitting diode stimulating ray sources and a diffusion plate positioned on the light emitting diode base plate and on which a gel including an electrophoresed specimen can be placed.

18. An image producing apparatus comprising:

at least one light emitting diode stimulating ray source;

filter means for cutting a stimulating ray emitted from the at least one light emitting diode stimulating ray source, and allowing only fluorescent light generated by stimulation of a fluorescent substance by the stimulating ray to pass; and a solid state image sensor for detecting the fluorescent light transmitted through the filter means;

wherein the at least one light emitting diode stimulating ray source comprises a light emitting diode base plate including a plurality of light emitting diode stimulating ray sources and a diffusion plate positioned on the light emitting diode base plate and on which an electrophoresis tank for accommodating a gel containing a specimen to be electrophoresed can be placed.

19. An image producing apparatus comprising:

at least one light emitting diode stimulating ray source;

filter means for cutting a stimulating ray emitted from the at least one light emitting diode stimulating ray source, and allowing only fluorescent light generated by stimulation of a fluorescent substance by the stimulating ray to pass; and a solid state image sensor for detecting the fluorescent light transmitted through the filter means;

wherein the at least one light emitting diode stimulating ray source is constituted as a blue light emitting diode for emitting a stimulating ray whose center wavelength is between 400 nm and 500 nm;

wherein the at least one light emitting diode stimulating ray source comprises a light emitting diode base plate including a plurality of light emitting diode stimulating ray sources and a diffusion plate positioned on the light emitting diode base plate and on which an electrophoresis tank for accommodating a gel containing a specimen to be electrophoresed can be placed.

20. A fluorescent image visualizing device comprising:

a blue light emitting diode array base plate including a plurality of light emitting diodes each adapted for emitting a stimulating ray having a center wavelength in the range of 400 nm to 500 nm;

a bandpass filter disposed on the base plate;

a diffusion plate disposed on the bandpass filter; and an electrophoresis tank positioned over the bandpass filter.

* * * * *